US010321836B2

(12) United States Patent
Walker et al.

(10) Patent No.: US 10,321,836 B2
(45) Date of Patent: Jun. 18, 2019

(54) CONTEXT SCORES TO ENHANCE ACCURACY OF ECG READINGS

(71) Applicant: Physio-Control, Inc., Redmond, WA (US)

(72) Inventors: Robert G. Walker, Seattle, WA (US); Daniel W. Piraino, Seattle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 14 days.

(21) Appl. No.: 15/365,938

(22) Filed: Nov. 30, 2016

(65) Prior Publication Data

US 2018/0146874 A1 May 31, 2018

Related U.S. Application Data

(60) Provisional application No. 62/261,231, filed on Nov. 30, 2015.

(51) Int. Cl.
*A61N 1/39* (2006.01)
*A61B 5/04* (2006.01)
*A61B 5/0408* (2006.01)
*A61B 5/00* (2006.01)

(52) U.S. Cl.
CPC ...... *A61B 5/04012* (2013.01); *A61B 5/04085* (2013.01); *A61B 5/7203* (2013.01); *A61N 1/3904* (2017.08); *A61N 1/3925* (2013.01)

(58) Field of Classification Search
None
See application file for complete search history.

(56) References Cited

U.S. PATENT DOCUMENTS

| 5,257,621 | A  | * | 11/1993 | Bardy | A61N 1/3621 600/518 |
| 8,805,482 | B2 | * | 8/2014  | Sitzman | A61B 5/04017 600/509 |
| 2006/0241701 | A1 | * | 10/2006 | Markowitz | A61N 1/025 607/5 |
| 2014/0364755 | A1 | * | 12/2014 | Sankai | A61B 7/02 600/513 |
| 2016/0192887 | A1 | * | 7/2016  | Sun | A61B 5/7221 702/19 |

* cited by examiner

*Primary Examiner* — Kennedy Schaetzle
(74) *Attorney, Agent, or Firm* — Lane Powell PC

(57) ABSTRACT

The present disclosure encompasses an "artifact score" derived from the signal characteristics of an acquired 12-lead ECG, (2) a "patient context score" derived from key elements of the patient's history, presentation, and prehospital emergency care, and (3) techniques for integrating these scores into an emergency medical care system.

10 Claims, 4 Drawing Sheets

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF EXTERNAL DEFIBRILLATORS

*Fig. 3* COMPONENTS OF EXTERNAL DEFIBRILLATOR

US 10,321,836 B2

CONTEXT SCORES TO ENHANCE ACCURACY OF ECG READINGS

CROSS REFERENCE TO RELATED APPLICATIONS

This patent application claims the benefit of and priority to U.S. Provisional Patent Application Ser. No. 62/226,231 filed on Nov. 30, 2015, entitled "Design and System Integration of 12-Lead ECG 'Context Scores' to Enhance Accuracy and Usability of Pre-Hospital 12-Lead ECGs," the disclosure of which is hereby incorporated by reference for all purposes.

BACKGROUND INFORMATION

It is well known that a leading cause of death is heart disease. One of the most serious incidences of heart disease is an ST Elevated Myocardial Infarction (STEMI), commonly known as a heart attack. Heart attacks are often, although not always, sudden and critical. Urgent medical attention is typically required for the sufferer to have a reasonable chance at survival.

Medical professionals have several ways of detecting the occurrence of a STEMI. One common method is the use of an electrocardiogram (ECG) to evaluate the heart rhythm of the patient, often at the scene where the patient is first encountered. The ECG is typically measured using some form of mobile heart monitor (e.g., a portable defibrillator or defibrillator/monitor). Modern medical devices both measure the patient's heart rhythm and automatically interpret the ECG data to perform a machine diagnosis of the patient's heart condition. Accordingly, modern medical devices are configured to automatically interpret the patient's heart rhythm to diagnose certain abnormalities, such as a STEMI. If a STEMI is indicated, the treating individual (e.g., an EMT, paramedic, or first responder) typically notifies an urgent care facility that a STEMI patient will be arriving shortly. In response, most urgent care facilities will prepare a catheterization laboratory or "cath lab" to treat the patient.

A cath lab is an examination room in a hospital or clinic with diagnostic imaging equipment used to visualize the arteries of the heart and the chambers of the heart and treat any stenosis or abnormality found. Cath labs are critically important to the effective treatment of a STEMI patient. However, they are also extremely expensive and resource-consuming to prepare for use. Activating a cath lab for a patient who is not actually experiencing a STEMI is very wasteful. Accordingly, false positive and false negative cath lab activations triggered by misinterpreted pre-hospital 12-lead ECGs cause patient harm, hospital resource waste, and customer dissatisfaction.

Improvements in the proper diagnosis of a patient experiencing STEMI or other urgent cardiac abnormalities are constantly being sought. Reducing false diagnoses of STEMI may reduce wasteful expenditures of time and resources treating a STEMI patient who is not actually experiencing STEMI.

SUMMARY OF THE DISCLOSURE

The disclosure is directed at performing an analysis to assist in determining a likelihood that a STEMI diagnosis is accurate. Generally stated, embodiments are directed at a method for diagnosis a cardiac condition, including:

capturing electrocardiogram data indicative of a cardiac condition of a patient;

performing an automated analysis of the electrocardiogram data to identify a possible diagnosis of the cardiac condition;

performing a second analysis of the electrocardiogram data to generate a qualitative value associated with the electrocardiogram data, the qualitative value being associated with a likelihood that the electrocardiogram data accurately reflects the cardiac condition of the patient; and providing an indication of the likelihood in conjunction with the possible diagnosis of the cardiac condition of the patient.

DETAILED DESCRIPTION OF EMBODIMENTS

Embodiments are disclosed that at least address certain problems with misdiagnosis of STEMI. Generally stated, embodiments are directed at systems and methods for providing a "context score" that may be used, either in an automated fashion or manually, to indicate a likelihood that a STEMI diagnosis is correct. Various criteria may be evaluated to influence the context score.

The disclosed embodiments couple a 12-lead ECG (and/or the automated interpretation derived from the 12-lead ECG) used in cardiac care medical devices with meaningful context about the likelihood that an initial diagnosis is wrong to allow any downstream person or process using the results of that 12-lead ECG to better gauge the degree of confidence that should be placed in the 12-lead ECG results, and the actions that should or shouldn't be taken based on those results.

Embodiments of the present disclosure implement techniques to provide valuable context to help interpret and decide actionability of a 12-lead ECG, or its derived automated interpretive statement, or both. In addition, disclosed are methods for integrating these context elements into an emergency medical care system, which may include vital-signs monitors or monitor/defibrillators, data telecommunication functionality, patient encounter documentation tools, and post-event data review and QA/QI tools.

This disclosure is structured as follows: First, an illustrative medical device is disclosed in which embodiments may be implemented. Next, specific embodiments of context scores are disclosed that provide insight to inform possible diagnosis based on a 12-lead ECG reading. Finally, specific embodiments of methods are described to employ context scores into an emergency medical care system.

Description of Operative Environment for Embodiments

Figures 1, 2:
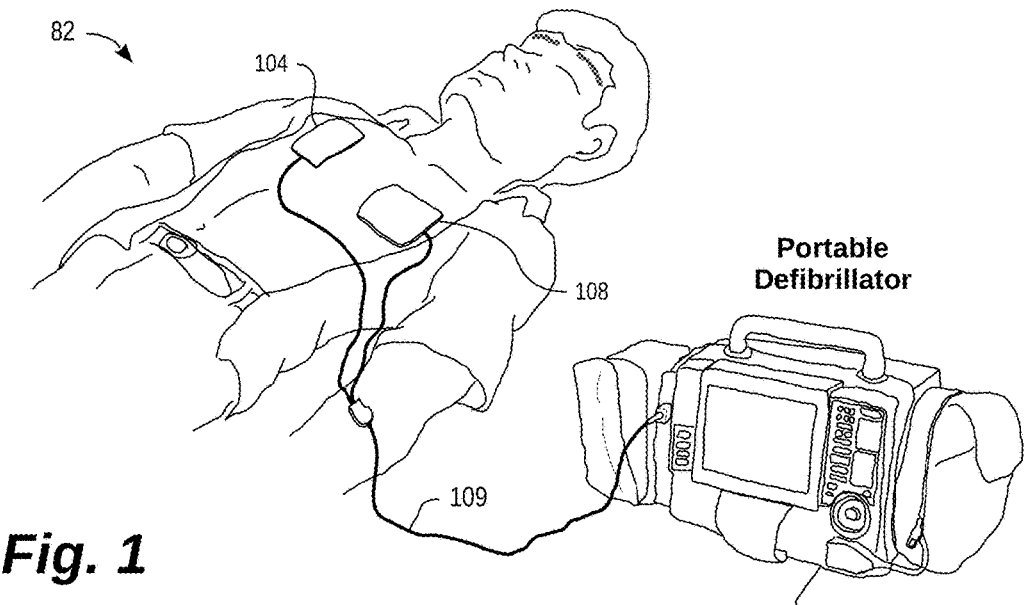
FIG. 1 is a diagram of a scene where an external defibrillator is used to try and save the life of a person in accordance with an embodiment.
FIG. 2 is a table listing two main types of the external defibrillator shown in FIG. 1, and by whom they might be used.

FIG. 1 is a diagram of a defibrillation scene. A person 82 is lying supine. Person 82 could be a patient in a hospital or someone found unconscious. Person 82 is experiencing a medical emergency, which could be, by way of an example, Ventricular Fibrillation (VF).

A portable external defibrillator 100 has been brought close to person 82. The portable external defibrillator can also be a hybrid monitor/defibrillator 82. At least two defibrillation electrodes 104, 108 are usually provided with external defibrillator 100. Electrodes 104, 108 are coupled with external defibrillator 100 via electrode leads 109. A rescuer (not shown) has attached electrodes 104, 108 to the skin of person 82. Defibrillator 100 is monitoring cardiac rhythms and potentially administering, via electrodes 104, 108, a brief, strong electric pulse through the body of person 82. The pulse, also known as a defibrillation shock, goes through the person's heart in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing examples of types of external defibrillators and their primary intended users. A first type of defibrillator 100 is generally called a defibrillator-monitor (or monitor-defibrillator) because it is typically formed as a single unit in combination with a patient monitor. Alternatively, the defibrillator-monitor may be a modular device with separable components. For example, in one alternative embodiment, the defibrillator-monitor may include a base component and a plurality of detachable pods or modules. Each pod communicates with the base component, perhaps wirelessly. Certain pods may be used to collect information about a patient, such as vital statistics. One example of such an alternative system is described in U.S. Pat. No. 8,738,128 entitled "Defibrillator/Monitor System Having A Pod With Leads Capable Of Wirelessly Communicating," the disclosure of which is hereby incorporated by reference for all purposes. A defibrillator-monitor is intended to be used by medical professionals, such as doctors, nurses, paramedics, emergency medical technicians, etc. Such a defibrillator-monitor is generally intended to be used in a pre-hospital or hospital scenario.

As a defibrillator, the device can be one of different varieties, or even versatile enough to be able to switch among different modes that individually correspond to the varieties. One variety is that of an automated external defibrillator (AED), which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals, such as a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data. In some embodiments, a patient monitor device does not include defibrillation functions and may optionally include other functions such as, for example, blood marker testing functionality, ventilation functionality, airway management functionality, CPR feedback functionality, and/or chest compression functionality.

A second type of external defibrillator 100 is generally called an AED, An AED typically makes the shock/no shock determination by itself, automatically. It can typically sense enough physiological conditions of the person 82 using only the defibrillation electrodes 104, 108 shown in FIG. 1. An AED can either administer the shock automatically, or instruct the user to do so, e.g. by pushing a button.

There are other types of external defibrillators in addition to those listed in FIG. 2. For example, a hybrid defibrillator can have aspects of an AED and also of a defibrillator-monitor. A usual such aspect is additional ECG monitoring capability.

Figure 3:
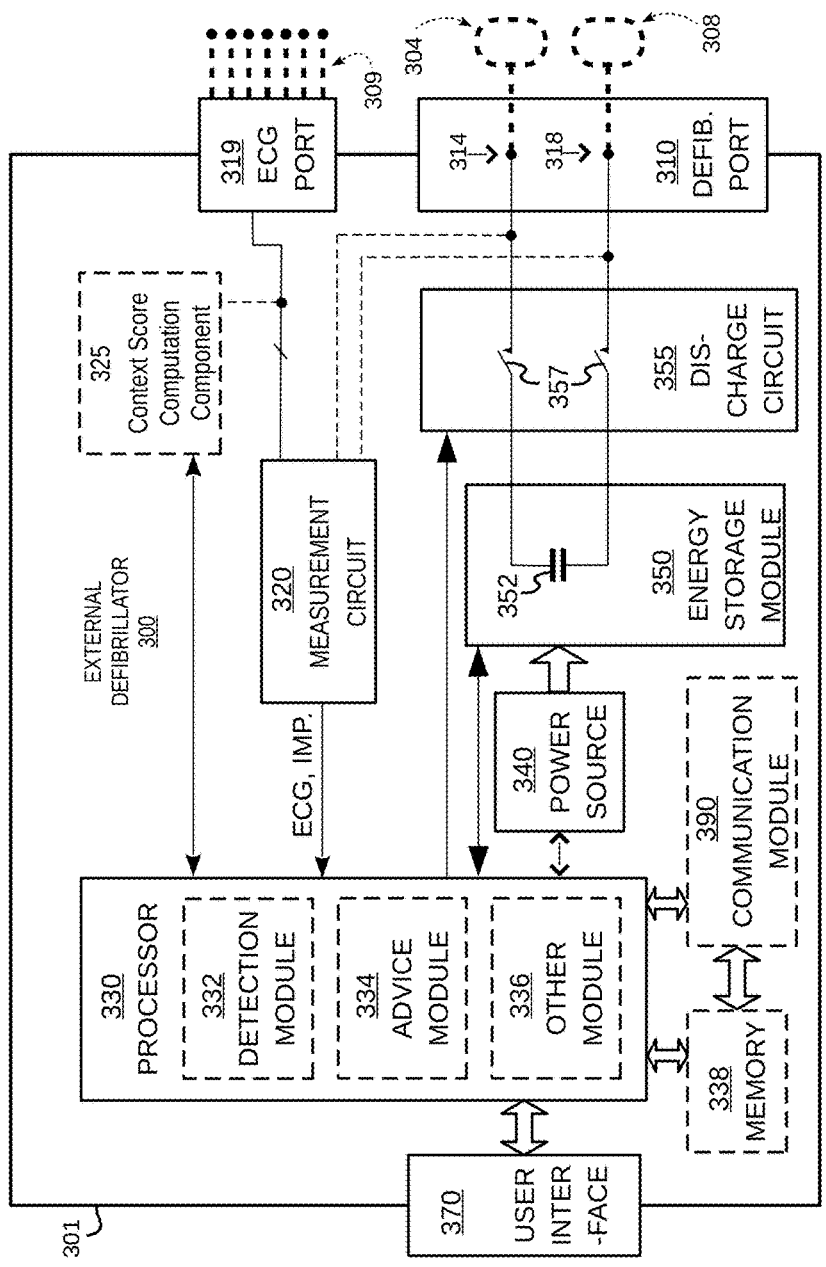
FIG. 3 is a diagram showing components of an external defibrillator made according to embodiments.

FIG. 3 is a diagram showing components of an external defibrillator 300 made according to embodiments. These components can be, for example, in external defibrillator 100 of FIG. 1. The components shown in FIG. 3 can be provided in a housing 301, also known as a casing. It will be appreciated that, in other embodiments, these components may be implemented in separate housings or as sub-components of various other devices.

External defibrillator 300 is intended for use by a user, who is frequently the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding an electrical charge to person 82 via electrodes 304, 308. The electrical charge may be stored in defibrillator 300, as discussed below.

If defibrillator 300 is a defibrillator-monitor, as was described with reference to FIG. 2, it will frequently also have an ECG port 319 in housing 301, for plugging in ECG lead wires 309. ECG lead wires 309 can sense an ECG signal, such as any of the ECG lead signals that comprise a common 12-lead ECG recording. Although frequently referred to as a 12-lead ECG throughout this document, other types of ECG lead signals are equally applicable. The use of the common term "12-lead" or "12-lead ECG" is merely for convenience and simplicity of discussion, and is not to be viewed as limiting. A defibrillator-monitor could have additional ports that are not shown.

Defibrillator 300 may also include a measurement circuit 320, which receives physiological signals from ECG port 319, and also from other ports, if provided. These physiological signals are sensed, and information about them is rendered by measurement circuit 320 as data, or other signals, etc.

Defibrillator 300 also includes a processor 330, which may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF. Another such module in processor 330 can be an advice module 334, which arrives at advice based on outputs of detection module 332. The advice can be to shock, to not shock, to administer other forms of therapy, and so on. If the advice is to shock, the AED will automatically charge the energy storage module 350. Some external defibrillator embodiments merely report the shock advice to the user, and prompt them to do it. Other embodiments further execute the advice, by administering the shock automatically. If the advice is to administer CPR, defibrillator 300 may further issue prompts for it, and so on. Processor 330 can include additional modules, such as other module 336, for other functions too numerous to list here.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. In addition, memory 338 can store prompts for the user, etc. Moreover, memory 338 can store patient data, such as, for example, data regarding how much fluid may have been administered to patient 82 as detected by the flow monitor component 325.

In one embodiment, the defibrillator 300 includes a "context score" component 325. In one specific implementation, the context score component 325 includes functions which, when executed by processor 330, operate to compute a value which may be used in a qualitative analysis of a diagnosis derived from ECG signals. For instance, if ECG signals collected via ECG port 319 are used in a machine-generated diagnosis of a patient's heart condition, the context score component 325 may perform a qualitative analysis of that diagnosis based on, for example, characteristics of the ECG signals. The qualitative analysis may then result in a report which may be output via user interface 370, described below.

Defibrillator 300 typically also includes a power source 340. To enable portability of defibrillator 300, power source 340 typically includes a battery. Such a battery is typically implemented as a battery pack, which can be rechargeable or not. Sometimes, a combination of rechargeable and non-rechargeable battery packs is used. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, or the like.

Defibrillator 300 moreover includes a discharge circuit 355. Discharge circuit 355 can be controlled to permit some or all of the energy stored in module 350 to be discharged to nodes 314, 318, and thus also to defibrillation electrodes 304, 308. Discharge circuit 355 can include one or more relays or switches 357. Those can be made in a number of ways, such as by an H-bridge, or the like.

Defibrillator 300 further includes a user interface 370. User interface 370 can be made in any number of ways. For example, interface 370 may include a screen, to display what is detected and measured, provide visual feedback to a rescuer for their resuscitation attempts, and so on. User interface 370 may also include a speaker to issue audible signals, such as voice prompts, or the like. The user interface 370 may issue prompts to the user, visually or audibly, so that the user can administer CPR, for example. Interface 370 may additionally include various controls, such as pushbuttons, keyboards, touch screens, and so on. In addition, discharge circuit 355 can be controlled by processor 330, or directly by user via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

"ECG Artifact Context Score"

Figure 4:
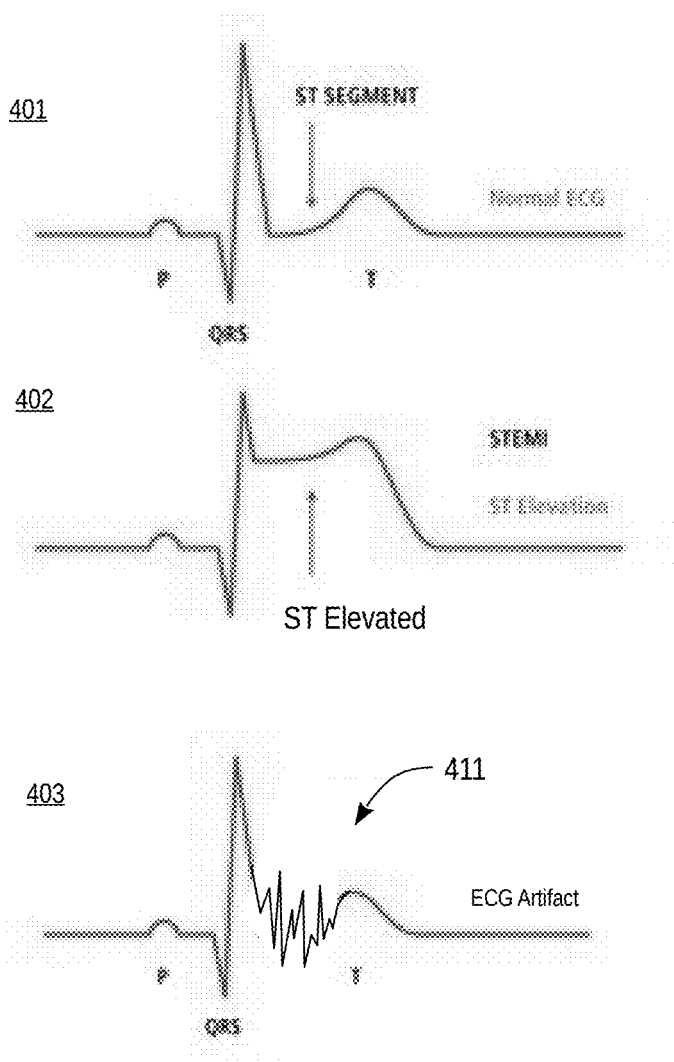
FIG. 4 is a conceptual illustration of various types of ECG traces.
Figure 5:
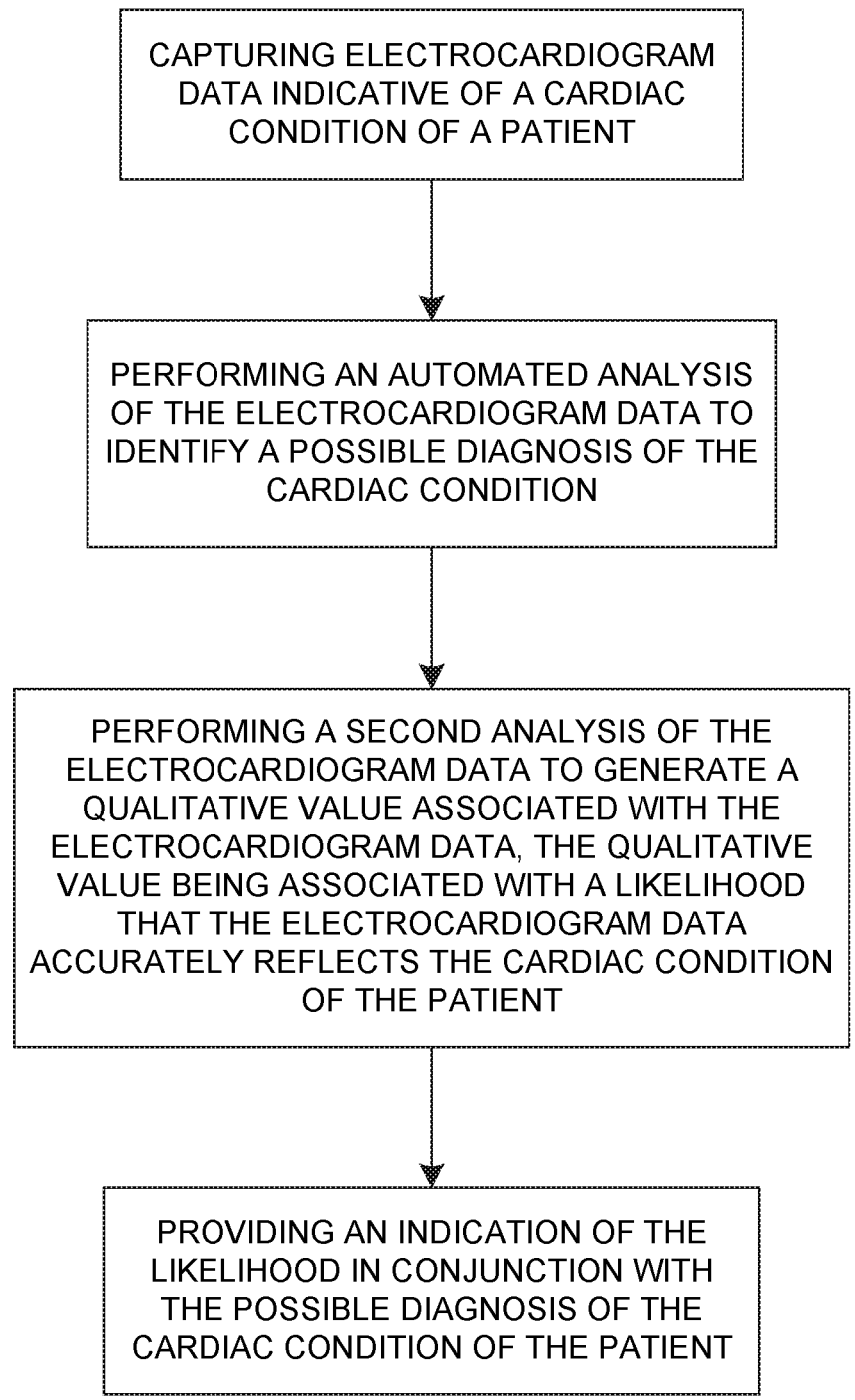
FIG. 5 is a functional flow diagram of a method of performing a qualitative analysis on a potential diagnosis of a patient experiencing a cardiac event.

One common contributing factor to false positive and false negative STEMI detections, particularly by automated 12-lead interpretation algorithms, is artifact in the ECG signal. Turning briefly to FIG. 4, three conceptual ECG traces are shown: a normal ECG 401, an ECG of a patient experiencing STEMI 402, and an ECG of an otherwise normal ECG 403 but which has significant ECG artifact 411. ECG artifacts are distorted signals caused by a secondary internal or external source, such as muscle movement or interference from an electrical device. As will be appreciated by those skilled in the art, the ECG artifact 411 may confuse an auto-generated analysis of the ECG into concluding that the artifact 411 actually represents an ST elevated signal, and thus an incorrect diagnosis of STEMI.

There are strategies to minimize artifact and optimize ECG acquisition conditions, but paramedics frequently eschew such strategies for the sake of saving time or coping with the circumstances of the patient care event. Accordingly, ECG artifact is a very common occurrence in ECG traces captured by first responders treating a cardiac patient.

In accordance with this disclosed embodiment, ECG artifact is quantified via signal processing means, and can thus be turned in to a numeric or categorical index representative of the magnitude/severity of artifact contamination of the acquired ECG. In one specific embodiment, the context score component 325 evaluates the presence and nature of artifacts occurring throughout the ECG. The presence of significant artifacts may indicate that an auto-generated diagnosis of STEMI may be unreliable and should be reviewed manually. Alternatively, the absence of significant ECG artifact may indicate that an auto-generated diagnosis of STEMI is likely accurate.

In an enhanced embodiment, the index is designed to represent the probability that the apparent interpretation of the 12-lead is confounded by the magnitude/severity of the artifact, and or the nature of the artifact. This enhanced embodiment takes advantage of the insight that some apparent interpretations of the ECG may be more or less susceptible to potential corruption by the type or amount of artifact present than others.

In one example, an extensive anterior STEMI with tombstoning may be confidently discernable despite a large amount of motion and/or muscle artifact, whereas a borderline STEMI may be exquisitely sensitive to even moderate motion or muscle artifact even if just one lead is affected. Thus, the apparent interpretation of the 12-lead can be used to modify/combine with the raw "artifact score" to produce a resultant probability or "believability" of that apparent interpretation. It will be appreciated that such a scheme can be applied both to situations where the emergency care system relies strictly on the results of the automated 12-lead interpretative algorithm, as well as to situations where the emergency care system involves pre-hospital provider interpretation of the 12-lead ECG. In the latter scenario, the probability/believability score produced based on the automated 12-lead interpretive algorithm would provide just as useful context for a provider-interpreted 12-lead as a machine-interpreted 12-lead.

"Patient Context Score"

Another potential contributing factor to false positive and false negative STEMI detections is statistical in nature. Overtesting for a condition that has low prevalence in a general population is guaranteed to produce false positive detections, since no test can be 100% accurate. Stated differently, the lower the pre-test probability that a given patient has a given condition (STEMI for example), the higher the probability of a false positive detection. In some EMS systems, paramedics are judicious about which patients they take 12-leads on, while in other EMS systems, paramedics will "take a 12-lead on any patient with a chest." Individual paramedics will also vary in their use of 12-lead ECGs within a given EMS system.

Emergency medicine confronts the challenge of low-prevalence conditions with concomitant overtesting risk with numerous other disease states, such as pulmonary embolism. One embodiment of the disclosure pairs a diagnostic test with a clinical decision rule or instrument that either recommends for/against performing the test, or provides additional context to help interpret or gauge actionability of the result of the diagnostic test. The "patient context score" is constructed, for example, using numeric scores assigned to the presence/absence of key elements of the patient's history, presentation, and/or prehospital emergency care (e.g. risk factors, symptoms, medications, etc), summed to produce a composite score.

Many or all of the data elements used to create the patient context score may already have been documented early during the patient contact in an electronic patient care documentation system. Thus embodiments of this disclosure incorporate automatically obtaining pertinent data elements from the electronic documentation, reducing the amount of dedicated data entry needed to produce the score.

"Repeated ECG Context Score"

Yet another factor to consider when assessing the quality of a cardiac diagnosis is the extent to which a current ECG agrees or disagrees with prior ECGs, if any. More specifically, a context score may be based on the number of 12-lead ECGs that have been taken during the patient encounter prior to the currently considered one. The results of multiple 12-leads (e.g., STEMI positive/negative, or STEMI positive/borderline/negative) can also be incorporated into a "Repeated ECG Context Score" patient context component. For example, if the paramedic has taken 12 STEMI-negative 12-leads, but the subsequent ECG reading produces a borderline positive result, the fact that 12 prior ECGs had been acquired with negative results is potentially valuable context suggesting the borderline positive result may be more likely to be a false positive than if that result had been obtained on a first ECG. Conversely, a non-borderline positive STEMI interpretation, obtained three times in a row, may suggest the positive result is even more believable and actionable than if only one ECG had produced that result.

Integrating Context Elements into an Emergency Medical Care System:

The several context scores just described may be used individually or in various combinations. Examples are numerous, and include the following:

Real-time display for the provider obtaining the 12-lead.

Incorporated into an algorithm recommending whether or not the 12-lead should be transmitted (or the results verbally communicated) to a remote destination. This can be more applicable to the artifact score.

Incorporated into an algorithm determining whether the 12-lead should be acted upon (e.g. direct activation of a cath lab) without any ECG overread or other input from a more senior medical provider (e.g. ED physician, consulting cardiologist).

Printed on the 12-lead image/printout.

Recorded in the patient care documentation.

Derived from printed on the 12-lead image/printout a QA/QI "dashboard" can facilitate system optimization. Since the patient care documentation would have the name of the provider who obtained the 12-lead, along with the artifact score and patient context score, a report/dashboard could be created showing aggregate scores for different providers over a period of time. This would allow a system to identify whether artifact or overtesting are common problems, as well as identify whether there are specific providers who could benefit from more training or focus on optimal 12-lead practices.

The score(s) could be transmitted in conjunction with the 12-lead through a the Lifenet system, and stored by Physio-Control, tagged with key non-PHI information such as date, agency, device type/serial number, configuration, etc. It should be noted that these scores could be transmitted into the Lifenet system for Physio-Control to record, even if they are not transmitted through the system to a customer final destination. The scores could even be transmitted into the Lifenet system (e.g. via Lifenet Asset) even if the 12-leads themselves are not transmitted through the Lifenet system. The accumulated database of artifact scores and patient context scores could be valuable for:

a. investigation of customer complaints
b. proactive communication with customers who may have significant unrecognized performance issues in their system (e.g. "we noticed that an inordinate number of your 12-leads have excessive artifact scores. We know that can compromise the accuracy of the diagnosis, and here are some tools and strategies that could help you"),
c. [Per artifact score] creating an automated "registry" of aggregate artifact scores accessible by customers, allowing customers to benchmark themselves against their anonymized peer agencies, thus creating a competitive marketplace incenting all customers to improve their 12-lead ECG quality, benefiting the patients, the customers, etc.

In summary, the disclosed embodiments overcome shortcomings of existing systems by obviating the need to either manually attempt to detect a pulse (which can be unreliable) and eliminating any need to align an ultrasound transducer with a vein or artery of the patient's heart. In these and other ways, which will become apparent upon a study of the disclosed teachings, these embodiments provide a superior treatment technique and transducer assembly for the detection of ROSC in a patient experiencing a cardiac incident.

Other embodiments may include combinations and subcombinations of features described above or shown in the Figures, including, for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, "feature" or "features" can refer to structures and/or functions of an apparatus, article of manufacture or system, and/or the steps, acts, or modalities of a method.

In the foregoing description, numerous details have been set forth in order to provide a sufficient understanding of the described embodiments. In other instances, well-known features have been omitted or simplified to not unnecessarily obscure the description. A person skilled in the art in view of this description will be able to practice the disclosed teachings. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, embodiments may be implemented in combination with other systems.

In general, the various features and processes described above may be used independently of one another, or may be combined in different ways. For example, this disclosure includes other combinations and sub-combinations equivalent to: extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations irrespective of other features in relation to which it is described. All possible combinations and subcombinations are intended to fall within the scope of this disclosure.

Certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example examples. The example systems and components described herein may be configured differently than described. For example, elements may be added to, removed from, or rearranged compared to the disclosed example examples. The following claims define certain combinations and subcombinations of elements, features, steps, and/or functions, which are regarded as novel and non-obvious. Additional claims for other combinations and subcombinations may be presented in this or a related document.

What is claimed is:

1. A method for treating a cardiac condition, comprising:
capturing electrocardiogram data;
automatically analyzing electrocardiogram data to identify electrocardiogram data indicative of a cardiac condition;
performing a second analysis of the electrocardiogram data;
generating an artifact score associated with the electrocardiogram data based on a magnitude/severity of an artifact identified by the second analysis and a comparison of the artifact to one or more predetermined artifact conditions associated with one or more numerical or categorical values, the artifact score being associated with a likelihood that the electrocardiogram data is accurately indicative of the cardiac condition;
outputting an indication of the likelihood and a diagnosis of the cardiac condition; and
treating the cardiac condition based on the indicated likelihood.

2. The method recited in claim 1, wherein the artifact score is further based on physiological characteristics of the patient other than the cardiac condition of the patient.

3. The method of claim 1, wherein the electrocardiogram data is captured via a 12-lead electrocardiogram coupled to a medical device.

4. The method of claim 3, wherein the captured electrocardiogram data and the artifact score are presented together on a display of the medical device.

5. The method of claim 3, wherein the electrocardiogram data is transmitted to a remote location by the medical device based on the artifact score.

6. The method of claim 1, further including:
determining a confidence score of the diagnosis of the cardiac condition; and
generating a cardiac condition likelihood score based on the confidence score and the artifact score, the cardiac condition likelihood indicative of a probability that the identified cardiac condition is present in the electrocardiogram data.

7. The method of claim 6, wherein the electrocardiogram data is captured via a 12-lead electrocardiogram coupled to a medical device.

8. The method of claim 6, further comprising transmitting the electrocardiogram data to a remote location based on the cardiac condition likelihood score.

9. The method of claim 6, further comprising transmitting an instruction to print the captured electrocardiogram data and one or more of the artifact score, the confidence score and the cardiac condition likelihood score.

10. The method of claim 1 further including:
generating a patient context score based on one or more of a history of a patient from whom the electrocardiogram data is captured, patient data of a prior healthcare event of the patient, and a presentation of the patient; and
calculating an accuracy of the presence of the cardiac condition in the electrocardiogram data based at least in part on the patient context score.

* * * * *